United States Patent
Cannell et al.

(10) Patent No.: US 8,926,954 B2
(45) Date of Patent: Jan. 6, 2015

(54) WAVE COMPOSITION CONTAINING A BISULFITE COMPOUND, A SULFATE COMPOUND, AND A PHENOL

(75) Inventors: David W. Cannell, New Hope, PA (US); Christine Shin, Princeton, NJ (US); Karen M. Saiewitz, Belchertown, MA (US)

(73) Assignee: L'Oreal S.A. (FR)

( * ) Notice: Subject to any disclaimer, the term of this patent is extended or adjusted under 35 U.S.C. 154(b) by 566 days.

(21) Appl. No.: 12/700,030

(22) Filed: Feb. 4, 2010

(65) Prior Publication Data

US 2010/0202996 A1    Aug. 12, 2010

Related U.S. Application Data

(60) Provisional application No. 61/207,252, filed on Feb. 9, 2009.

(51) Int. Cl.

| | | |
|---|---|---|
| A61K 8/25 | (2006.01) | |
| A61Q 5/04 | (2006.01) | |
| A61K 8/23 | (2006.01) | |
| A61K 8/34 | (2006.01) | |
| A61K 8/365 | (2006.01) | |
| A61K 8/42 | (2006.01) | |
| A61K 8/97 | (2006.01) | |

(52) U.S. Cl.
CPC ... *A61Q 5/04* (2013.01); *A61K 8/23* (2013.01); *A61K 8/347* (2013.01); *A61K 8/365* (2013.01); *A61K 8/42* (2013.01); *A61K 8/97* (2013.01)
USPC .......................................... 424/70.5; 424/70.2

(58) Field of Classification Search
None
See application file for complete search history.

(56) References Cited

U.S. PATENT DOCUMENTS

| | | |
|---|---|---|
| 2,623,002 A | 12/1952 | Fricke |
| 3,966,903 A | 6/1976 | Torii et al. |
| 4,158,704 A | 6/1979 | Baer et al. |
| 4,214,596 A * | 7/1980 | Kaplan et al. ............... 132/204 |
| 4,228,810 A | 10/1980 | Moore et al. |
| 4,243,659 A * | 1/1981 | Balingit et al. ............ 424/70.5 |
| 4,841,997 A | 6/1989 | Petrow |
| 4,970,067 A | 11/1990 | Panandiker et al. |
| 5,294,230 A | 3/1994 | Wu et al. |
| 5,338,540 A | 8/1994 | Lee et al. |
| 5,474,578 A | 12/1995 | Chan et al. |
| 5,554,364 A | 9/1996 | Neill et al. |
| 5,589,177 A | 12/1996 | Herb et al. |
| 5,641,480 A | 6/1997 | Vermeer |
| 5,656,280 A | 8/1997 | Herb et al. |
| 5,942,216 A | 8/1999 | Herb et al. |
| 6,022,547 A | 2/2000 | Herb et al. |
| 6,855,312 B1 | 2/2005 | Craig et al. |
| 2001/0008031 A1 | 7/2001 | Schultz et al. |
| 2003/0125378 A1 | 7/2003 | Biatry et al. |
| 2003/0143172 A1 | 7/2003 | Ito et al. |
| 2005/0129652 A1 | 6/2005 | Keller et al. |
| 2006/0272103 A1 | 12/2006 | Barbarat |
| 2007/0166256 A1 * | 7/2007 | Shiroyama et al. .......... 424/70.2 |
| 2008/0044368 A1 | 2/2008 | Boumard et al. |
| 2009/0317349 A1 * | 12/2009 | Zaeska et al. ................ 424/70.2 |

FOREIGN PATENT DOCUMENTS

| | | | |
|---|---|---|---|
| CN | 1267212 A | | 9/2000 |
| CN | 1646084 A | | 7/2005 |
| CN | 1698573 A | | 11/2005 |
| DE | 19749164 A1 | * | 7/1998 |
| EP | 0190834 A2 | | 8/1986 |
| JP | 59-051209 | | 3/1984 |
| JP | 61-183213 | | 8/1986 |
| JP | 64-066109 | | 3/1989 |
| JP | 05-112432 B2 | | 5/1993 |
| JP | 2000229819 A | | 8/2000 |
| JP | 2003534389 A | | 11/2003 |

OTHER PUBLICATIONS

International Search Report and Written Opinion, PCT/US09/06716, dated Feb. 25, 2010.
Chinese Office Action for Application No. 200980153422.X dated Nov. 20, 2013.
Chinese Office Action for Application No. 2009801534.22 dated Feb. 22, 2013.
Chinese Office Action for Application No. 200980153422.X dated Jul. 28, 2014.

* cited by examiner

*Primary Examiner* — Ernst V Arnold
*Assistant Examiner* — Kyung Sook Chang
(74) *Attorney, Agent, or Firm* — Lerner, David, Littenberg, Krumholz & Mentlik, LLP

(57) ABSTRACT

Disclosed are waving compositions for waving of keratinous fibers, such as hair, containing a) a bisulfite compound, b) a sulfate compound or urea, and c) a phenol, and methods of waving keratinous fibers by applying such compositions to keratinous fibers. Also disclosed is a multi-unit cosmetic kit for treating a keratinous fiber containing a) a first unit containing a first composition containing a bisulfite compound and a sulfate compound or urea, and b) a second unit containing a second composition containing a phenol.

20 Claims, No Drawings

WAVE COMPOSITION CONTAINING A BISULFITE COMPOUND, A SULFATE COMPOUND, AND A PHENOL

CROSS-REFERENCE TO RELATED APPLICATIONS

This application claims the benefit of the filing date of U.S. Provisional Patent Application No. 61/207,252 filed Feb. 9, 2009, the disclosure of which is hereby incorporated herein by reference.

BACKGROUND OF THE INVENTION

Compositions for waving of hair contain a reducing agent for breaking the disulfide bonds in hair, thereby allowing the hair to be permanently reshaped. U.S. Pat. No. 4,158,704, for example, teaches methods for waving of hair using compositions containing thioglycolate compounds as the reducing agents. U.S. Pat. No. 5,554,364 teaches that thioglycolate compositions produce waving of hair that typically lasts about 2 to 4 months. However, mercaptans or thioglycolates produce a strong unpleasant odor.

U.S. Pat. No. 5,338,540 teaches hair waving compositions containing a sulfite and/or bisulfite reducing system, urea, and a cationic polyquaternary resin, which yield a hair waving or straightening effect equivalent to thioglycolate compositions, but without the unpleasant odors associated with thioglycolate. However, U.S. Pat. No. 5,474,578 teaches that bisulfites are known to strip color from artificially colored hair.

SUMMARY OF THE INVENTION

A first aspect of the present invention is directed to a waving composition for waving of keratinous fibers containing a) a bisulfite compound, b) a sulfate compound or urea, and c) a phenol. In certain embodiments, the compositions do not contain a thioglycolate as an additional reducing agent.

A second aspect of the present invention is directed to a method for waving of keratinous fibers by applying to a keratinous fiber a waving composition containing a) a bisulfite compound, b) a sulfate compound or urea, and c) a phenol. In certain embodiments, the methods do not include applying a thioglycolate as an additional reducing agent to the keratinous fibers.

A third aspect of the present invention is directed to a multi-unit cosmetic kit for treating keratinous fibers containing a) a first unit containing a first composition containing a bisulfite compound and a sulfate compound or urea, and b) a second unit containing a second composition containing a phenol.

Underlying the present invention is the discovery that the combination of a bisulfite compound, a sulfate compound or urea, and a phenol provides a waving composition having improved properties with regards to curl, wear, and color fading. The waving compositions of the present invention may be applied to keratinous fibers to produce a tight wave that may last for about to about 2 months with relatively little color fading. As illustrated in the working examples herein, embodiment(s) of the present invention exhibited unexpectedly less color fading compared to a commercial product that contains thioglycolates, or compared to compositions containing a bisulfite compound and a sulfate compound or urea, but not containing any phenol.

DETAILED DESCRIPTION

In the waving compositions of the present invention, the bisulfite compound acts as a reducing agent that breaks the disulfide bonds of the cysteine of the keratinous fiber. The bisulfite compounds useful to make the present invention are generally provided in the form of a cosmetically acceptable salt. In an embodiment of the present invention, the bisulfite compound employed in the compositions is in the form of an ammonium, alkanol amine, alkali metal, or alkali earth metal bisulfite salt, such as, ammonium bisulfite, monoethanolamine bisulfite, sodium bisulfite, potassium bisulfite, or calcium bisulfite.

The bisulfite compound, e.g., ammonium bisulfite, may be present in the compositions of the present invention in an amount that generally ranges from about 4% to about 20% by weight, and in some embodiments, from about 6% to about 18% by weight, based on the total weight of the cosmetic composition. In yet other embodiments, the amount of the bisulfite compound is about 6%, about 8%, or about 10% by weight, based on the total weight of the cosmetic composition.

The sulfate compounds useful in the present invention may also be provided in the form of a cosmetically acceptable salt, e.g., salts of weak bases. Suitable examples include ammonium sulfate, monoethanolamine lauryl sulfate, monoethanolamine laureth sulfate, and triethanolamine sulfate.

The sulfate compound may be present in the compositions of the present invention in an amount that generally ranges from about 0.1% to about 20% by weight, and in some embodiments, from about 0.2% to about 5% by weight, and in yet other embodiments, from about 0.4% to about 4% by weight, based on the total weight of the cosmetic composition. In certain embodiments, the amount of the sulfate compound is from about 1.0% to about 2.0% by weight, such as about 1.1%, 1.2%, 1.3%, 1.4%, 1.5%, 1.6%, 1.7%, 1.8%, or 1.9%, by weight, based on the total weight of the composition.

In some embodiments of the present invention, urea is present (with or without the sulfate compound). In the waving compositions of the present invention, urea causes swelling of the shaft of the keratinous fiber, thus facilitating penetration of the bisulfite compound into the keratinous fiber. Urea may be present in the compositions of the present invention in an amount that generally ranges from about 0.1% to about 20% by weight, and in some embodiments, from about 0.2% to about 10% by weight, and in yet other embodiments, from about 0.4% to about 5% by weight, based on the total weight of the composition. In certain embodiments, the amount of urea is from about 2% to about 3% by weight, such as about 2.1%, 2.2%, 2.3%, 2.4%, 2.5%, 2.6%, 2.7%, 2.8%, or 2.9% by weight, based on the total weight of the composition.

As used herein, the term "phenol" refers to a compound containing a six-membered aromatic ring bonded directly to a hydroxyl group. In an embodiment of the present invention, the phenolic compound is ferulic acid, phloretin, caffeic acid, myricitine, gallic acid, vanillic acid, phloroglucinol, phloridizin, hydroxy cinnamic acid, or pyrogallic acid. The phenol may be present in the compositions of the present invention in an amount that generally ranges from about 0.1% to about 10% by weight, and in some embodiments, from about 0.2% to about 8% by weight, and in yet other embodiments, from about 0.5% to about 4% by weight, based on the total weight of the composition. In some embodiments, the phenol is ferulic acid or phloretin and is present in an amount of about 4% by weight, based on the total weight of the composition.

In certain embodiments, the phenol may be a provided as part of a composition or extract, such as green tea extract, grape seed extract, or pomegranate extract. The composition or extract containing the phenol may be present in the compositions of the present invention in an amount that generally ranges from about 0.1% to about 10% by weight, and in some embodiments, from about 0.2% to about 8% by weight, and in yet other embodiments, from about 0.5% to about 4% by weight, based on the total weight of the composition. In some embodiments, the extract is green tea extract and is present in an amount of about 0.5% by weight, based on the total weight of the composition.

In certain embodiments, the compositions of the present invention further contain a silicone compound. In an embodiment of the present invention, the silicone compound is an aminosilicone, such as amodimethicone. The silicone compound may be present in the compositions of the present invention in an amount that generally ranges from about 0.1% to about 5% by weight, and in some embodiments, from about 0.2% to about 4% by weight, and in yet other embodiments, from about 0.5% to about 2% by weight, based on the total weight of the composition.

The exact nature of the composition is not critical. For example, depending (in part) on the amount of water that may be present, the waving composition may be in the form of an aqueous solution, dispersion, emulsion, or suspension. Thus, in certain embodiments, water is present in an amount of from about 0.1% to about 99% by weight, and in other embodiments, from about 50% to about 98% by weight, and in yet other embodiments, from about 50% to about 75% by weight, based on the total weight of the composition.

The waving compositions of the present invention may further contain a surfactant. Examples of surfactants that may be employed in the waving compositions of the present invention include amphoteric/zwitterionic surfactants, such as betaines, nonionic surfactants, anionic surfactants, and cationic surfactants. Suitable amphoteric surfactants include, for example, lauryl betaine, lauroamphoglycinate, lauroamphopropylsulfonate, lauroamphopropionate, lauroampho-carboxyglycinate, lauryl sultane, myristamidopropyl betaine, myristyl betaine, myristoamphoglycinate, myristyl propionate, stearoamphoglycinate, stearoamphopropionate, stearoamphopropylsulfonate, stearyl betaine, cocamidoethyl betaine, cocamidopropyl betaine, cocamidopropyl hydroxysultane, cocamidopropyl dimethylamine propionate, cocoamphoglycinate, cocoamphocarboxypropionate, cocoamphocarboxyglycinate, coco-betaine, cocoamphopropionate, and cocoamphopropylsulfonate, and combinations thereof.

Representative examples of nonionic surfactants include fatty acid esters and alkoxylated, particularly ethoxylated, fatty acid esters of polyhydric alcohols such as glycerols and sorbitol, for example, polyoxyethylene monolaurate, polyoxyethylene monooleate, polyoxyethylene monostearate, sorbitan monolaurate, sorbitan trioleate, generally with a degree of ethoxylation of from about 20 to about 85; mono- and di-alkanolamides, such as the N-acyl derivatives of mono- and di-ethanol amines, and polyethoxylated monoalkanolamides such as PEG-15 cocamide; amine oxides, such as cocamidopropyl dimethylamine oxides, coco bis-2-hydroxyethyl amine oxides and lauryl dimmethylamine oxide; ethoxylated alkanolamides; ethoxylated oils and fats such as ethoxylated lanolins; and ethoxylated alkylphenols, such as nonoxynol, and combinations thereof.

Representative examples of anionic surfactants include, alkylethercarboxylic acids, such as laureth-11 carboxylic acid, the alkali metal, ammonium, or amine salts of alkyl sulfates, alkyl ether sulfates, linear alpha-olefin sulfonates, dialkyl sulfosuccinates, alkylamidosulfosuccinates, and alkyl taurates each having from about $C_{12}$ to $C_{18}$ alkyl or alkenyl groups, and combinations thereof. Particular examples include the salts of lauryl sulfates and lauryl ether sulfates, the latter having an average level of ethoxylation of 1-3.

Representative examples of cationic surfactants include quaternium-16, quaternium-26, quaternium-27, quaternium-30, quaternium-33, quaternium-43, quaternium-52, quaternium-53, quaternium-56, quaternium-60, quaternium-61, quaternium-62, quaternium-70, quaternium-71, quaternium-72, quaternium-75, quaternium-76 hydrolyzed collagen, quaternium-77, quaternium-78, quaternium-79 hydrolyzed collagen, quaternium-79 hydrolyzed keratin, quaternium-79 hydrolyzed milk protein, quaternium-79 hydrolyzed silk, quaternium-79 hydrolyzed soy protein, and quaternium-79 hydrolyzed wheat protein, quaternium-80, quaternium-81, quaternium-82, quaternium-83, quaternium-84, and combinations thereof.

Surfactants are typically present in compositions of the present invention in amounts ranging from about 0.1% to about 5% by weight, and in some embodiments, from about 0.5% to about 3% by weight, based on the total weight of the composition.

The waving compositions of the present invention may further contain a chelating agent, such as an amine, carboxylic acid, phosphonic acid, or polyphosphoric acid, and metal salts thereof. Suitable examples of chelating agents include pentasodium penteate, edetic acid, glutamic tetraacetic acid, asparaginic tetraacetic acid, propyl diamine tetraacetic acid, and metal salts of such acids.

Chelating agents are generally present in amounts less than about 2% by weight, and in some other embodiments, less than about 1% by weight, based on the total weight of the composition.

The waving compositions of the present invention may further contain a swelling agent, also referred to herein as a penetration enhancer. Suitable swelling agents or penetration enhancers include lower alcohols and polyols, such as $C_1$ to $C_4$ alcohols and polyols. Representative examples of swelling agents or penetration enhancers include ethanol, propanol, isopropanol, 1,2-propylene glycol, 1,3-butanediol, glycerol, ethylcarbitol, benzyl alcohol, benzyloxyethanol, urea, and 2-methylpyrrolidone.

Swelling agents or penetration enhancers are generally present in amounts ranging from about 0.1% to about 10% by weight, and in some embodiments, from about 1% to about 5% by weight, based on the total weight of the composition.

The pH of the waving compositions of the present invention generally ranges from moderately acidic to moderately alkaline. Thus, in some other embodiments, the pH of the waving composition is in the range of about 5 to about 9, and in other embodiments, of about 7 to about 8. In some embodiments, the pH of the waving composition is about 7.

Thus, the waving compositions of the present invention may further contain a pH adjuster. Representative examples of pH adjusters include organic acids such as citric acid, malic acid, lactic acid, succinic acid and oxalic acid, sodium salts of the organic acids, and alkaline agents such as ammonia, monoethanolamine, diethanolamine, triethanolamine, sodium hydroxide, potassium hydroxide, sodium carbonate, sodium hydrogencarbonate, potassium carbonate and potassium hydrogencarbonate.

The waving compositions may further contain at least one additional auxiliary ingredient suitable for hair care. Examples of such ingredients are familiar to one of skill in the art and include solvents, structuring agents such as waxes and polymers, hydrophobic (lipophilic) and hydrophilic thickeners or gelling agents, skin conditioning agents, sunscreen agents (e.g., octocrylene, octinoxate, avobenzone), preservatives (e.g., sodium citrate, phenoxyethanol, parabens and mixtures thereof), cosmetic active agents and dermatological active agents such as, for example, hydrolyzed peptides, farnesol, bisabolol, phytantriol, aesthetic agents such as essential oils, fragrances, skin sensates, opacifiers, aromatic compounds (e.g., clove oil, menthol, camphor, eucalyptus oil, and eugenol), foam enhancers, botanical extracts, and anti-inflammatory agents.

To practice the methods of the present invention, the waving composition is applied to keratinous fibers (which may be natural or synthetic), such as hair, to maintain a desired shape. Typically, water is applied to the keratinous fibers and the wetted fibers are styled into a desired shape using well known techniques, e.g., wrapped around a rod. The waving composition of the present invention is then applied to the styled keratinous fibers, rinsed with water, and then dried.

The compositions of the present invention may be applied by hand. Alternatively, or in conjunction therewith, they may be applied via an applicator such as a sponge, cotton, brush or a puff of a natural or synthetic material. The applicator may be attached to a container that serves as a reservoir for the waving composition.

The waving composition is allowed to remain in contact with the keratinous fibers for a period of time sufficient to break disulfide bonds in the keratinous fibers to a sufficient degree to allow for waving. In embodiments of the present invention, the keratinous fibers are allowed to remain in contact with the waving composition for about 10 minutes to about 60 minutes, in other embodiments for, about 20 minutes to about 40 minutes, and in yet other embodiments, for about 25 minutes.

In an embodiment of the present invention, a neutralizer composition is applied to the keratinous fibers, typically after the waving composition has been rinsed from the keratinous fibers. The neutralizer composition stimulates reformation of the disulfide bonds in the keratinous fiber broken by the reducing agent in the waving composition. The result is that the hair is fixed in the desired shape for a longer period than if the neutralizer composition were not used. The keratinous fibers are allowed to remain in contact with the neutralizer composition for a period of time sufficient to allow the neutralizer composition to reform sufficient disulfide bonds in the keratinous fibers to allow for longer lasting waving. In an embodiment of the present invention, the keratinous fibers are in contact with the neutralizer composition for about 1 minute to about 20 minutes, in another embodiment, for about 2 minutes to about 10 minutes, and in yet another embodiment, for about 5 minutes. The neutralizer is then rinsed from the keratinous fibers with water and the keratinous fibers are dried to produce the desired shape.

The neutralizer composition of the present invention contains an oxidizing agent. Representative examples of oxidizing agents include peroxides, bromates, and perborates, e.g., hydrogen peroxide, potassium bromate, sodium bromate and sodium perborate.

In an embodiment of the present invention, the neutralizer composition is acidic and has a pH between about 2 and about 5, e.g., about 3. Thus, the neutralizer composition may also contain a pH adjuster such as phosphoric acid, a hair conditioning agent, such as a quaternary ammonium salt, e.g., dicetyldimonium chloride (commercially available from EVONIK Goldschmidt GmbH (Westfalen, Germany) under the tradename VARISOFT 432 CG®), or a siloxane, e.g., amodimethicone, a surfactant, such as a quaternary ammonium salt, e.g., cetrimonium chloride, or a polyethylene glycol ether of an alcohol, e.g., trideceth-12, and water. A mixture of 31% amodimethicone, 2.2% cetrimonium chloride, and 1.9% trideceth-12 is commercially available from Dow Corning (Midland, Mich.) under the tradename 949 CATIONIC EMULSION®.

The neutralizer composition may further contain at least one additional ingredient suitable for hair care. Examples of such ingredients are familiar to one of skill in the art and include chelating agents, swelling agents or penetration enhancers, solvents, emulsifiers, structuring agents such as waxes and polymers, hydrophobic (lipophilic) and hydrophilic thickeners or gelling agents, skin conditioning agents, sunscreen agents (e.g., octocrylene, octinoxate, avobenzone), preservatives (e.g., sodium citrate, phenoxyethanol, parabens and mixtures thereof), cosmetic active agents and dermatological active agents such as, for example, hydrolyzed peptides, farnesol, bisabolol, phytantriol, aesthetic agents such as essential oils, fragrances, skin sensates, opacifiers, aromatic compounds (e.g., clove oil, menthol, camphor, eucalyptus oil, and eugenol), foam enhancers, botanical extracts, and anti-inflammatory agents.

The multi-unit cosmetic kits of the present invention contain a first unit containing a bisulfite compound and urea or a sulfate compound, and a second unit containing a phenol. In use, the phenol is added to the bisulfite and urea or sulfate composition to form a waving composition of the present invention prior to its application to a keratinous fiber. In one embodiment, the bisulfite compound and urea or the sulfate compound in the first unit are provided in the form of an aqueous composition, and the phenol is provided in a dry form, such as a tablet, powder, or granule. The dry phenol is added to the aqueous composition and dissolved therein. In some embodiments, the cosmetic kit further includes a third unit containing the neutralizer composition.

The following examples are intended to further illustrate the present invention. They are not intended to limit the invention in any way. Unless otherwise indicated, all parts are by weight.

EXAMPLES

Example 1

Inventive Compositions

Waving compositions of the present invention were made as follows:

| Waving Composition Formula 1A: | |
| --- | --- |
| INGREDIENT | AMOUNT (Wt %) |
| PEG-15 Cocamine | 20 |
| Ferulic Acid | 4 |
| Ammonium Bisulfite | 10 |
| Pentasodium Pentatate | 0.16 |
| Ammonium Sulfate | 1.2 |
| Cocamidopropyl Betaine | 1.75 |
| Isopropanol | 2.0 |
| Monoethanol Amine | Adjust pH to 7.0 |
| Deionized Water | QS to 100 |

| Waving Composition Formula 1B:: | |
| --- | --- |
| INGREDIENT | AMOUNT (Wt %) |
| PEG-15 Cocamine | 20 |
| Ferulic Acid | 4 |
| Ammonium Bisulfite | 10 |
| Pentasodium Pentatate | 0.16 |
| Urea | 2.3 |
| Cocamidopropyl Betaine | 1.75 |

Waving Composition Formula 1B:

| INGREDIENT | AMOUNT (Wt %) |
| --- | --- |
| Isopropanol | 2.0 |
| Monoethanol Amine | Adjust pH to 7.0 |
| Deionized Water | QS to 100 |

To make waving compositions of Formulas 1A and 1B, PEG-15 cocamine and ferulic acid were premixed in a tank. Deionized water was heated to 80° C. and slowly added to the PEG-15 cocamine and ferulic acid premix. When the ferulic acid was completely dissolved and the mixture became clear and uniformly mixed, the remaining ingredients were added in the order listed while mixing until uniform between each addition. Monoethanol amine ("MEA") was added to adjust solution to pH 7.0. The solution was then QS to 100% with deionized water.

Example 2

Inventive Compositions

Waving compositions of the present invention were made as follows:

Waving Composition Formula 2A:

| INGREDIENT | AMOUNT (Wt %) |
| --- | --- |
| Laureth-11 Carboxylic Acid | 14.4 |
| PEG-15 Cocamine | 8.0 |
| Phloretin | 4.0 |
| Ammonium Bisulfite | 10 |
| Pentasodium Pentatate | 0.16 |
| Ammonium Sulfate | 1.2 |
| Cocamidopropyl Betaine | 1.75 |
| Isopropanol | 2.0 |
| Monoethanol Amine | Adjust pH to 7.0 |
| Deionized Water | QS to 100 |

Waving Composition Formula 2B:

| INGREDIENT | AMOUNT (Wt %) |
| --- | --- |
| Laureth-11 Carboxylic Acid | 14.4 |
| PEG-15 Cocamine | 8.0 |
| Phloretin | 4.0 |
| Ammonium Bisulfite | 10 |
| Pentasodium Pentatate | 0.16 |
| Urea | 2.3 |
| Cocamidopropyl Betaine | 1.75 |
| Isopropanol | 2.0 |
| Monoethanol Amine | Adjust pH to 7.0 |
| Deionized Water | QS to 100 |

To make waving compositions of Formulas 2A and 2B, laureth-11 carboxylic acid, PEG-15 cocamine, and phloretin were premixed in a tank. Deionized water was heated to 80° C. and slowly added to the laureth-11 carboxylic acid, PEG-15 cocamine, and phloretin premix. When the phloretin was completely dissolved and the mixture became clear and uniformly mixed, the remaining ingredients were added in the order listed while mixing until uniform between each addition. MEA was added to adjust solution to pH 7.0. The solution was then QS to 100% with deionized water.

Example 3

Inventive Compositions

Waving compositions of the present invention were made as follows:

Waving Composition Formula 3A:

| INGREDIENT | AMOUNT (Wt %) |
| --- | --- |
| Green Tea Extract | 0.5% |
| Ammonium Bisulfite | 10 |
| Pentasodium Pentatate | 0.16 |
| Ammonium Sulfate | 1.2 |
| Cocamidopropyl Betaine | 1.75 |
| Isopropanol | 2.0 |
| Monoethanol Amine | Adjust pH to 7.0 |
| Deionized Water | QS to 100 |

Waving Composition Formula 3B:

| INGREDIENT | AMOUNT (Wt %) |
| --- | --- |
| Green Tea Extract | 0.5% |
| Ammonium Bisulfite | 10 |
| Pentasodium Pentatate | 0.16 |
| Urea | 2.3 |
| Cocamidopropyl Betaine | 1.75 |
| Isopropanol | 2.0 |
| Monoethanol Amine | Adjust pH to 7.0 |
| Deionized Water | QS to 100 |

To make waving compositions of Formulas 3A and 3B, deionized water was heated in a tank to 80° C. and the green tea extract was added. When the green tea extract was completely dissolved and the mixture became clear and uniformly mixed, the remaining ingredients were added in the order listed while mixing until uniform between each addition. MEA was added to adjust solution to pH 7.0. The solution was then QS to 100% with deionized water.

Example 4

Comparative Compositions

Comparative compositions lacking the phenol were made as follows:

Comparative Composition Formula 4A:

| INGREDIENT | AMOUNT (Wt %) |
| --- | --- |
| Ammonium Bisulfite | 10 |
| Pentasodium Pentatate | 0.16 |
| Ammonium Sulfate | 1.2 |
| Cocamidopropyl Betaine | 1.75 |
| Isopropanol | 2.0 |
| Monoethanol Amine | Adjust pH to 7.0 |
| Deionized Water | QS to 100 |

| Comparative Composition Formula 4B: | |
| --- | --- |
| INGREDIENT | AMOUNT (Wt %) |
| Ammonium Bisulfite | 10 |
| Pentasodium Pentatate | 0.16 |
| Urea | 2.3 |
| Cocamidopropyl Betaine | 1.75 |
| Isopropanol | 2.0 |
| Monoethanol Amine | Adjust pH to 7.0 |
| Deionized Water | QS to 100 |

To make waving compositions of Formulas 4A and 4B, deionized water was loaded into a tank and the ingredients were added in the order listed. MEA was used to adjust pH to 7.0. The solution was then QS to 100% with deionized water.

Example 5

The inventive waving compositions of Examples 1-3, the comparative compositions of Example 4, and a commercially available waving composition containing ammonium thioglycolate were each evaluated and compared using 2 colored hair swatches as follows:

Method for Coloring Hair Swatches:

Artificially colored hair swatches for testing were produced using the following method. Natural white hair swatches were obtained, measuring 1 cm wide, 14 cm long, and weighing 2.8 g, were dyed with Color Fusion™ 5VR (Redken (New York, N.Y.)) with Pro-oxide 20 vol developer at 1:1 ratio, and processed for 30 minutes. Each swatch was then shampooed for 35 seconds and rinsed well for 25 seconds with water at 40° C.

Method for Treating Hair Swatches and Measuring Color Change:

The colored hair swatches were air-dried and measured for an initial color reading using Konica Minolta Spectrophotometer with SpectraMagic™ software. This initial color reading was compared to a value obtained for each swatch after treatment.

Two strips of the artificially colored hair swatches were placed on a weight boat and enough of the appropriate waving or comparative formula was added to the weight boat to immerse the swatches. Swatches were immersed for 25 minutes and rinsed with water at 40° C. for 3 minutes. Swatches were then towel-blotted and placed on another weigh boat. Enough of the hydrogen-peroxide based neutralizer, described below, was added the weight boat to immerse the hair swatches. The swatches were immersed in the neutralizer for 5 minutes.

A hydrogen peroxide neutralizer was produced having the following formula:

| INGREDIENT | AMOUNT (Wt %) |
| --- | --- |
| Deionized water | QS to 100 |
| Hydrogen Peroxide | 1.6-2.40% |
| Varisoft 432 CG ® | 0.50% |
| Dow Corning 949 Cationic Emulsion ® | 2.00% |
| Phosphoric Acid | Adjust pH to 3.0 |

Deionized water was added to a tank. The ingredients were then added to the tank in the order listed above. Phosphoric acid was added to adjust the pH of the solution to 3.0. The solution was then QS to 100% with deionized water.

Swatches were then rinsed with 40° C. water for 3 minutes. The swatches were air-dried and measured for color readings using Konica Minolta® Spectrophotometer to measure a color reading. According to this system, the overall color change from the initial to the final (after-treatment) color reading, ΔE, was calculated using standard techniques used with this apparatus. For purposes of the present invention, a difference in ΔE values of at least 3 is considered as a statistically significant difference in color retention.

| Formula | Average ΔE |
| --- | --- |
| Waving Composition Formula 1A | 13.6 |
| Waving Composition Formula 1B | 15.8 |
| Waving Composition Formula 2A | 9.88 |
| Waving Composition Formula 2B | 15.2 |
| Waving Composition Formula 3A | 15.0 |
| Waving Composition Formula 3B | 19.0 |
| Comparative Composition 4A | 16.2 |
| Comparative Composition 4B | 22.0 |
| Thioglycolate Waving Composition | 30.7 |

The results show that swatches treated with the inventive waving compositions containing a phenol retained more color compared to swatches treated with the comparative compositions without the phenol, and compared to a commercial product containing thioglycolate.

Method for Preparing and Treating Colored Test Curl Swatches ("Curl Samples") to Evaluate Curl:

Using the artificially colored hair swatches, curl samples were made by gluing 20 strands of artificially colored hair that were 4 7/16 inches in length. Five (5) curl samples wrapped around a curing rod were placed on a weight boat and immersed in the appropriate waving or comparative composition. The curl samples were processed for 25 minutes and rinsed with 40° C. water for 3 minutes.

The curl samples were then towel-blotted, placed in a weight boat, and neutralized by immersion in the hydrogen peroxide neutralizer for 5 minutes. The curl samples were then rinsed with 40° C. water for 3 minutes. The curl samples were taken out of the rods and air-dried.

The length of each of the curled swatches was measured and an average taken.

| Formula | Average Curl Length (cm) |
| --- | --- |
| Waving Composition Formula 1A | 7.80 |
| Waving Composition Formula 1B | 7.92 |
| Waving Composition Formula 2A | 8.14 |
| Waving Composition Formula 2B | 7.98 |
| Waving Composition Formula 3A | 8.24 |
| Waving Composition Formula 3B | 7.64 |
| Comparative Composition 4A | 7.34 |
| Comparative Composition 4B | 7.68 |

The results show that curl samples treated with the inventive waving compositions containing a phenol had comparable curl length compared to comparative compositions without the phenol.

Example 6

Waving compositions of the present invention with 6% and 8% ammonium bisulfite are made having the following formulas using the same procedure described in Example 1.

| INGREDIENT | Formula 6A | Formula 6B | Formula 6C | Formula 6D |
|---|---|---|---|---|
| PEG-15 Cocamine | 20 | 20 | 20 | 20 |
| Ferulic Acid | 4 | 4 | 4 | 4 |
| Ammonium Bisulfite | 6 | 8 | 6 | 8 |
| Pentasodium Pentatate | 0.16 | 0.16 | 0.16 | 0.16 |
| Ammonium Sulfate | 1.2 | 1.2 | — | — |
| Urea | — | — | 2.3 | 2.3 |
| Cocamidopropyl Betaine | 1.75 | 1.75 | 1.75 | 1.75 |
| Isopropanol | 2.0 | 2.0 | 2.0 | 2.0 |
| Monoethanol Amine | Adjust pH to 7.0 | Adjust pH to 7.0 | Adjust pH to 7.0 | Adjust pH to 7.0 |
| Deionized Water | QS to 100 | QS to 100 | QS to 100 | QS to 100 |

Example 7

Waving compositions of the present invention with 6% and 8% ammonium bisulfite are made having the following formulas using the same procedure described in Example 2.

| INGREDIENT | Formula 7A | Formula 7B | Formula 7C | Formula 7D |
|---|---|---|---|---|
| Laureth-11 Carboxylic Acid | 14.4 | 14.4 | 14.4 | 14.4 |
| PEG-15 Cocamine | 8.0 | 8.0 | 8.0 | 8.0 |
| Phloretin | 4.0 | 4.0 | 4.0 | 4.0 |
| Ammonium Bisulfite | 6.0 | 8.0 | 6.0 | 8.0 |
| Pentasodium Pentatate | 0.16 | 0.16 | 0.16 | 0.16 |
| Ammonium Sulfate | 1.2 | 1.2 | — | — |
| Urea | — | — | 2.3 | 2.3 |
| Cocamidopropyl Betaine | 1.75 | 1.75 | 1.75 | 1.75 |
| Isopropanol | 2.0 | 2.0 | 2.0 | 2.0 |
| Monoethanol Amine | Adjust pH to 7.0 | Adjust pH to 7.0 | Adjust pH to 7.0 | Adjust pH to 7.0 |
| Deionized Water | QS to 100 | QS to 100 | QS to 100 | QS to 100 |

Example 8

Waving compositions of the present invention with 6% and 8% ammonium bisulfite are made having the following formulas using the same procedure described in Example 3.

| INGREDIENT | Formula 8A | Formula 8B | Formula 8C | Formula 8D |
|---|---|---|---|---|
| Green Tea Extract | 0.5% | 0.5% | 0.5% | 0.5% |
| Ammonium Bisulfite | 6.0 | 8.0 | 6.0 | 8.0 |
| Pentasodium Pentatate | 0.16 | 0.16 | 0.16 | 0.16 |
| Ammonium Sulfate | 1.2 | 1.2 | — | — |
| Urea | — | — | 2.3 | 2.3 |
| Cocamidopropyl Betaine | 1.75 | 1.75 | 1.75 | 1.75 |
| Isopropanol | 2.0 | 2.0 | 2.0 | 2.0 |
| Monoethanol Amine | Adjust pH to 7.0 | Adjust pH to 7.0 | Adjust pH to 7.0 | Adjust pH to 7.0 |
| Deionized Water | QS to 100 | QS to 100 | QS to 100 | QS to 100 |

Example 9

Waving compositions of the present invention with 0.5%, 1.0%, or 2.0% ferulic acid are made having the following formulas using the same procedure described in Example 1.

| INGREDIENT | Formula 9A | Formula 9B | Formula 9C | Formula 9D | Formula 9E | Formula 9F |
|---|---|---|---|---|---|---|
| PEG-15 Cocamine | 20.0 | 20.0 | 20.0 | 20.0 | 20.0 | 20.0 |
| Ferulic Acid | 0.5 | 1.0 | 2.0 | 0.5 | 1.0 | 2.0 |
| Ammonium Bisulfite | 10.0 | 10.0 | 10.0 | 10.0 | 10.0 | 10.0 |
| Pentasodium Pentatate | 0.16 | 0.16 | 0.16 | 0.16 | 0.16 | 0.16 |
| Ammonium Sulfate | 1.2 | 1.2 | 1.2 | — | — | — |
| Urea | — | — | — | 2.3 | 2.3 | 2.3 |
| Cocamidopropyl Betaine | 1.75 | 1.75 | 1.75 | 1.75 | 1.75 | 1.75 |
| Isopropanol | 2.0 | 2.0 | 2.0 | 2.0 | 2.0 | 2.0 |
| Monoethanol Amine | Adjust pH to 7.0 | Adjust pH to 7.0 | Adjust pH to 7.0 | Adjust pH to 7.0 | Adjust pH to 7.0 | Adjust pH to 7.0 |
| Deionized Water | QS to 100 | QS to 100 | QS to 100 | QS to 100 | QS to 100 | QS to 100 |

Example 10

Waving compositions of the present invention with 0.5%, 1.0%, or 2.0% phloretin are made having the following formulas using the same procedure described in Example 2.

| INGREDIENT | AMOUNT (Wt %) | | | | | |
|---|---|---|---|---|---|---|
| | Formula 10A | Formula 10B | Formula 10C | Formula 10D | Formula 10E | Formula 10F |
| Laureth-11 Carboxylic Acid | 14.4 | 14.4 | 14.4 | 14.4 | 14.4 | 14.4 |
| PEG-15 Cocamine | 8.0 | 8.0 | 8.0 | 8.0 | 8.0 | 8.0 |
| Phloretin | 0.5 | 1.0 | 2.0 | 0.5 | 1.0 | 2.0 |
| Ammonium Bisulfite | 10.0 | 10.0 | 10.0 | 10.0 | 10.0 | 10.0 |
| Pentasodium Pentatate | 0.16 | 0.16 | 0.16 | 0.16 | 0.16 | 0.16 |
| Ammonium Sulfate | 1.2 | 1.2 | 1.2 | — | — | — |
| Urea | — | — | — | 2.3 | 2.3 | 2.3 |
| Cocamidopropyl Betaine | 1.75 | 1.75 | 1.75 | 1.75 | 1.75 | 1.75 |
| Isopropanol | 2.0 | 2.0 | 2.0 | 2.0 | 2.0 | 2.0 |
| Monoethanol Amine | Adjust pH to 7.0 | Adjust pH to 7.0 | Adjust pH to 7.0 | Adjust pH to 7.0 | Adjust pH to 7.0 | Adjust pH to 7.0 |
| Deionized Water | QS to 100 | QS to 100 | QS to 100 | QS to 100 | QS to 100 | QS to 100 |

Example 11

Waving compositions of the present invention with 1.0%, 2.0%, or 4.0% green tea extract are made having the following formulas using the same procedure described in Example 3.

| INGREDIENT | AMOUNT (Wt %) | | | | | |
|---|---|---|---|---|---|---|
| | Formula 11A | Formula 11B | Formula 11C | Formula 11D | Formula 11E | Formula 11F |
| Green Tea Extract | 1.0 | 2.0 | 4.0 | 1.0 | 2.0 | 4.0 |
| Ammonium Bisulfite | 10.0 | 10.0 | 10.0 | 10.0 | 10.0 | 10.0 |
| Pentasodium Pentatate | 0.16 | 0.16 | 0.16 | 0.16 | 0.16 | 0.16 |
| Ammonium Sulfate | 1.2 | 1.2 | 1.2 | — | — | — |
| Urea | — | — | — | 2.3 | 2.3 | 2.3 |
| Cocamidopropyl Betaine | 1.75 | 1.75 | 1.75 | 1.75 | 1.75 | 1.75 |
| Isopropanol | 2.0 | 2.0 | 2.0 | 2.0 | 2.0 | 2.0 |
| Monoethanol Amine | Adjust pH to 7.0 | Adjust pH to 7.0 | Adjust pH to 7.0 | Adjust pH to 7.0 | Adjust pH to 7.0 | Adjust pH to 7.0 |
| Deionized Water | QS to 100 | QS to 100 | QS to 100 | QS to 100 | QS to 100 | QS to 100 |

Example 12

Waving compositions of the present invention with 0.5%, 1.0%, or 2.0% amodimethicone are made having the following formulas using the same procedure described in Example 1.

| INGREDIENT | AMOUNT (Wt %) | | | | | |
|---|---|---|---|---|---|---|
| | Formula 12A | Formula 12B | Formula 12C | Formula 12D | Formula 12E | Formula 12F |
| PEG-15 Cocamine | 20.0 | 20.0 | 20.0 | 20.0 | 20.0 | 20.0 |
| Ferulic Acid | 4.0 | 4.0 | 4.0 | 4.0 | 4.0 | 4.0 |
| Ammonium Bisulfite | 10.0 | 10.0 | 10.0 | 10.0 | 10.0 | 10.0 |
| Pentasodium Pentatate | 0.16 | 0.16 | 0.16 | 0.16 | 0.16 | 0.16 |
| Ammonium Sulfate | 1.2 | 1.2 | 1.2 | — | — | — |
| Urea | — | — | — | 2.3 | 2.3 | 2.3 |
| Cocamidopropyl Betaine | 1.75 | 1.75 | 1.75 | 1.75 | 1.75 | 1.75 |
| Isopropanol | 2.0 | 2.0 | 2.0 | 2.0 | 2.0 | 2.0 |
| Amodimethicone | 0.5 | 1.0 | 2.0 | 0.5 | 1.0 | 2.0 |
| Monoethanol Amine | Adjust pH to 7.0 | Adjust pH to 7.0 | Adjust pH to 7.0 | Adjust pH to 7.0 | Adjust pH to 7.0 | Adjust pH to 7.0 |
| Deionized Water | QS to 100 | QS to 100 | QS to 100 | QS to 100 | QS to 100 | QS to 100 |

The amodimethicone is provided as part of the composition Wacker-Belsil ADM Log 1® (Wacker Chemie AG (Munich, Germany)), which consists of amodimethicone at 15%, Glycerin at 3.5%, Trideceth-5 at 6% and Trideceth-10 at 1.5%.

Example 13

Waving compositions of the present invention with 0.5%, 1.0%, or 2.0% amodimethicone are made having the following formulas using the same procedure described in Example 2.

| INGREDIENT | AMOUNT (Wt %) | | | | | |
|---|---|---|---|---|---|---|
| | Formula 13A | Formula 13B | Formula 13C | Formula 13D | Formula 13E | Formula 13F |
| Laureth-11 Carboxylic Acid | 14.4 | 14.4 | 14.4 | 14.4 | 14.4 | 14.4 |
| PEG-15 Cocamine | 8.0 | 8.0 | 8.0 | 8.0 | 8.0 | 8.0 |
| Phloretin | 4.0 | 4.0 | 4.0 | 4.0 | 4.0 | 4.0 |
| Ammonium Bisulfite | 10.0 | 10.0 | 10.0 | 10.0 | 10.0 | 10.0 |
| Pentasodium Pentatate | 0.16 | 0.16 | 0.16 | 0.16 | 0.16 | 0.16 |
| Ammonium Sulfate | 1.2 | 1.2 | 1.2 | — | — | — |
| Urea | — | — | — | 2.3 | 2.3 | 2.3 |
| Cocamidopropyl Betaine | 1.75 | 1.75 | 1.75 | 1.75 | 1.75 | 1.75 |
| Isopropanol | 2.0 | 2.0 | 2.0 | 2.0 | 2.0 | 2.0 |
| Amodimethicone | 0.5 | 1.0 | 2.0 | 0.5 | 1.0 | 2.0 |
| Monoethanol Amine | Adjust pH to 7.0 | Adjust pH to 7.0 | Adjust pH to 7.0 | Adjust pH to 7.0 | Adjust pH to 7.0 | Adjust pH to 7.0 |
| Deionized Water | QS to 100 | QS to 100 | QS to 100 | QS to 100 | QS to 100 | QS to 100 |

The amodimethicone is provided as part of the composition Wacker-Belsil ADM Log 1®.

Example 14

Waving compositions of the present invention with 0.5%, 1.0%, or 2.0% amodimethicone are made having the following formulas using the same procedure described in Example 3.

| INGREDIENT | AMOUNT (Wt %) | | | | | |
|---|---|---|---|---|---|---|
| | Formula 14A | Formula 14B | Formula 14C | Formula 14D | Formula 14E | Formula 14F |
| Green Tea Extract | 0.5% | 0.5% | 0.5% | 0.5% | 0.5% | 0.5% |
| Ammonium Bisulfite | 10.0 | 10.0 | 10.0 | 10.0 | 10.0 | 10.0 |
| Pentasodium Pentatate | 0.16 | 0.16 | 0.16 | 0.16 | 0.16 | 0.16 |
| Ammonium Sulfate | 1.2 | 1.2 | 1.2 | — | — | — |
| Urea | — | — | — | 2.3 | 2.3 | 2.3 |
| Cocamidopropyl Betaine | 1.75 | 1.75 | 1.75 | 1.75 | 1.75 | 1.75 |
| Isopropanol | 2.0 | 2.0 | 2.0 | 2.0 | 2.0 | 2.0 |
| Amodimethicone | 0.5 | 1.0 | 2.0 | 0.5 | 1.0 | 2.0 |
| Monoethanol Amine | Adjust pH to 7.0 | Adjust pH to 7.0 | Adjust pH to 7.0 | Adjust pH to 7.0 | Adjust pH to 7.0 | Adjust pH to 7.0 |
| Deionized Water | QS to 100 | QS to 100 | QS to 100 | QS to 100 | QS to 100 | QS to 100 |

The amodimethicone is provided as part of the composition Wacker-Belsil ADM Log 1®.

All publications cited in the specification, both patent publications and non-patent publications, are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A waving composition for waving of a keratinous fiber comprising:
   a) a bisulfite compound, which is present in an amount from 10 to about 18% by weight, based on the total weight of the composition;
   b) a sulfate compound or urea, wherein the sulfate compound is present in an amount of 1 to about 2% by weight, or wherein the urea is present in an amount of 2.0 to about 3.0%, based on the total weight of the composition; and
   c) a phenol, which is present in an amount of 0.5 to about 4% by weight, based on the total weight of the composition.

2. The composition according to claim 1, wherein the bisulfite compound is ammonium bisulfite.

3. The composition according to claim 1, wherein the sulfate compound is ammonium sulfate.

4. The composition according to claim 1, wherein the phenol is ferulic acid.

5. The composition according to claim 1, wherein the phenol is phloretin.

6. The composition according to claim 1, wherein the composition comprises green tea extract comprising the phenol.

7. The composition according to claim 1, further comprising a silicone compound.

8. The composition according to claim 7, wherein the silicone compound is amodimethicone.

9. The composition according to claim 1, comprising a) ammonium bisulfite, b) ammonium sulfate or urea, and c) ferulic acid, phloretin, or green tea extract.

10. The composition according to claim 1 or 8, further comprising a surfactant, a chelating agent, a swelling agent or penetration enhancer, a pH adjuster, and water.

11. The composition according to claim 10, wherein said surfactant is cocamidopropyl betaine.

12. The composition according to claim 10, wherein said chelating agent is pentasodium pentetate.

13. The composition according to claim 10, wherein said swelling agent or penetration enhancer is isopropanol.

14. The composition according to claim 10, wherein said pH adjuster is monoethanolamine.

15. A method for waving a keratinous fiber comprising applying to a keratinous fiber a waving composition comprising:
   a) a bisulfite compound, which is present in an amount from 10 to about 18% by weight, based on the total weight of the composition;
   b) a sulfate compound or urea, wherein the sulfate compound or urea is present in an amount of 1 to about 2% by weight, or wherein the urea is present in an amount of 2.0 to about 3.0%, based on the total weight of the composition; and
   c) a phenol, which is present in an amount of 0.5 to about 4% by weight, based on the total weight of the composition.

16. The method according to claim 15, further comprising applying a neutralizer composition to the keratinous fiber after applying the waving composition to the keratinous fiber.

17. The method according to claim 15, wherein the keratinous fiber is not treated with any thioglycolate compound or composition.

18. A multi-unit cosmetic kit for treating a keratinous fiber comprising:
- a) a first unit containing a first composition comprising a bisulfite compound and a sulfate compound or urea, and
- b) a second unit containing a second composition comprising a phenol,
- such that upon mixing to form a waving composition, the bisulfite compound is present in an amount of 10 to 18% by weight, the sulfate compound is present in an amount of 1.0 to about 2.0%, or wherein the urea is present in an amount of 2 to about 3% by weight, and the phenol is present in an amount of 0.5 to about 4% by weight, each based on the total weight of the waving composition.

19. The kit according to claim 18, further comprising: c) a third unit containing a neutralizer composition.

20. A method of making a waving composition for waving of a keratinous fiber comprising mixing together:
- a) a bisulfite compound, which is present in an amount from 10 to about 18% by weight, based on the total weight of the composition;
- b) a sulfate compound or urea, wherein the sulfate compound is present in an amount of 1.0 to about 2.0%, or wherein the urea is present in an amount of 2.0 to about 3.0% by weight, based on the total weight of the composition; and
- c) a phenol, which is present in an amount of 0.5 to about 4% by weight, based on the total weight of the composition.

* * * * *